United States Patent [19]

Appelgren et al.

[11] Patent Number: 5,081,154
[45] Date of Patent: Jan. 14, 1992

[54] METOPROLOL SUCCINATE

[75] Inventors: Curt H. Appelgren, Kungsbacka; Eva C. Eskilsson, Mölnlycke, both of Sweden

[73] Assignee: Aktiebolaget Hassle, Molndal, Sweden

[21] Appl. No.: 590,237

[22] Filed: Sep. 28, 1990

Related U.S. Application Data

[63] Continuation of Ser. No. 172,897, Mar. 25, 1988, Pat. No. 5,001,161.

[30] Foreign Application Priority Data

Jan. 10, 1984 [SE]  Sweden .............................. 8400085

[51] Int. Cl.$^5$ .................. A61K 31/045; A61K 31/19; A61K 31/20
[52] U.S. Cl. .................................... 514/651; 514/652; 514/925
[58] Field of Search ........................ 514/651, 925, 652

[56] References Cited

U.S. PATENT DOCUMENTS 3,873,600  3/1975  Brandstrom et al. ............... 568/565
4,256,752  3/1981  von Bebenburg et al. ......... 514/925

OTHER PUBLICATIONS

Gould, P. L., "Salt Selection for Basic Drugs", Int. J. Pharm. 33 (1986), 201–217.

Ragnarsson et al., "Development of a New Controlled Release Metoprolol Product", Drug Devel. and Indus. Pharmacy, 13, 9-11 (1987), 1495-1509.

Primary Examiner—Ronald W. Griffin
Attorney, Agent, or Firm—White & Case

[57] ABSTRACT

The present invention relates to metoprolol succinate, a new therapeutically active compound, and pharmaceutical preparations comprising this new compound.

1 Claim, No Drawings

METOPROLOL SUCCINATE

This application is a continuation of application Ser. No. 172,897, filed on Mar. 25, 1988, now U.S. Pat. No. 5,001,161, issued Mar. 19, 1991.

DESCRIPTION

1. Technical Field

The present invention relates to a new oral, therapeutically active compound, which can be released in the gastrointestinal tract below the upper part of the small intestine.

The object of the present invention is to obtain a therapeutically active compound intended to be released close to or within the colon, and particularly to such active compounds which are soluble in the pH range 1 to 8.

2. Background of the Invention

There exists an everlasting problem within pharmacy to be able to adminster a therapeutically active compound as close as possible to the colon, or preferably in the colon in order to thereby to eliminate the risk for acidic influence on the active compound by the gastric juice, or to prevent from irritation of the ventricular mucous membrane due to a reflux, or to obtain a therapeutically effectin the lower part of the gastrointestinal tract.

As suitable active compounds is has previously been proposed propanolol, alprenolol, and metoprolol tartrate, quinidine sulphate, quinidine bisulphate, quinidine hydrochloride, furosemide, and 5aminosalicyclic acid, i.e., such weak bases or salts thereof, the pH of which is 1 to 8.

DESCRIPTION OF THE PRESENT INVENTION

It has now surprisingly been shown possibel to be able to use, for this purpose, a previously unknown compound, viz. metoprolol succinate.

The metoprolol succinate has a melting point of 136°–137° C.

This compound can, in order to be administered orally be treated in accordance with the method proposed in EP-A1-0 040 590. Herein it has been proposed an oral pharmaceutical composition comprising a core containing a therapeutically active compound, which core has been coated with a layer comprising 10 to 85% by weight of an anionic polymer soluble at a pH above 5.5, and 15 to 90% by weight of a waterinsoluble polymer selected from the group of quaternary ammonium subsituted acrylic polymers.

From the point of view of flavor and/or identification o flavoured or coloured layer can optionally be applied outside the rleease controlling layer. This is, however, no part of the present invention.

When dosing the ready made product a number of discrete, coated particles/granules corresponding to a therapeutical dose unit of the actual therapeutical compound is administered.

When administering, in order to achieve a steady blood plasma level of the therapeutically active compound, a split dose unit of the therapeutically active compound provided with a coating according to the present invention can be administered together with some particles/granules which are not coated.

The particles are normally packed in small envelopes, tubular containers, or other capsules comprising a dose unit of a therapeutically active compound.

We claim:
1. Metoprolol succinate.
* * * * *

Disclaimer 5,081,154—Curt H. Appelgren, Kungsbacka; Eva C. Eskilsson, Molnlycke, both of Sweden. METOPROLOL SUCCINATE. Patent dated Jan. 14, 1992. Disclaimer filed May 9, 2003, by the assignee, Aktiebolaget Hassle.

The term of this patent shall not extend beyond the expiration date of Pat. No. 5,001,161.

*(Official Gazette, October 28, 2003)*

UNITED STATES PATENT AND TRADEMARK OFFICE
CERTIFICATE OF CORRECTION

PATENT NO. : 5,081,154  Page 1 of 1
DATED : January 14, 1992
INVENTOR(S) : Curt H. Appelgren et al.

It is certified that error appears in the above-identified patent and that said Letters Patent is hereby corrected as shown below:

Title page,
Item [63], Related U.S. Application Data: "5,001,161" should read -- 5,001,161, which is a continuation-in-part of Application No. 06/690,197, filed January 10, 1985, Patent No. 4,780,318 --.

Column 1,
Line 6, "Mar. 19, 1991" should read -- Mar. 19, 1991, which is a continuation-in-part of Application No. 06/690,197 filed January 10, 1985, Patent No. 4,780,318 --.

Signed and Sealed this

Sixteenth Day of March, 2004

JON W. DUDAS
*Acting Director of the United States Patent and Trademark Office*

Disclaimer

5,081,154 — Curt H. Applegren, Kungsbacka; Eva C. Eskilsson, Molnlycke, both of Sweden. METROPROLOL SUCCINATE. Patent dated Jan. 14, 1992. Disclaimer Filed Jan. 26, 2005, by the Assignee, AstraZeneca Limited Partnership.

The term of this patent subsequent to the patent number 4,975,745 has been disclaimed.

*(Official Gazette May 10, 2005)*